United States Patent [19]

Sieber

[11] Patent Number: 4,775,625
[45] Date of Patent: Oct. 4, 1988

[54] INACTIVATING ENVELOPED VIRUSES WITH A MEROCYANINE DYE

[75] Inventor: Fritz Sieber, Brookfield, Wis.

[73] Assignee: The Medical College of Wisconsin, Inc., Milwaukee, Wis.

[21] Appl. No.: 933,697

[22] Filed: Nov. 21, 1986

[51] Int. Cl.[4] .......................... C12N 7/00; C12N 7/06
[52] U.S. Cl. ...................................... 435/238; 424/3; 424/89; 514/274; 544/300; 544/319
[58] Field of Search ....................... 435/238; 514/274; 544/300, 319; 424/89, 3

[56] References Cited

U.S. PATENT DOCUMENTS

| | | | |
|---|---|---|---|
| 4,321,919 | 3/1982 | Edelson | 128/214 R |
| 4,398,906 | 8/1983 | Edelson | 604/6 |
| 4,424,201 | 1/1984 | Valinsky et al. | 424/3 |
| 4,428,744 | 1/1984 | Edelson | 604/6 |
| 4,464,166 | 8/1984 | Edelson | 604/6 |
| 4,568,328 | 2/1986 | King | 604/6 |
| 4,573,960 | 3/1986 | Goss | 604/6 |
| 4,573,961 | 3/1986 | King | 604/6 |
| 4,573,962 | 3/1986 | Troutner | 604/6 |
| 4,578,056 | 3/1986 | King et al. | 604/6 |
| 4,596,547 | 6/1986 | Troutner | 604/4 |
| 4,623,328 | 11/1986 | Hartranft | 604/4 |

FOREIGN PATENT DOCUMENTS

124363 7/1984 European Pat. Off. .

OTHER PUBLICATIONS

Sims et al., Biochemistry, 13(16): 3315-3330 (1974).
Sieber et al., Proc. Nat'l Acad. Sci., U.S.A., 81: 7584-7587 (1984).
Journal of Cellular Physiology, 116: 118-124 (1983), "Susceptibility to Merocyanine 540-Mediated Photosensitization: A Differentiation Marker on Murine Hematopoietic Progenitor Cells," Meagher et al.
Proc. Natl. Acad. Sci., U.S.A., vol. 81, pp. 7584-7587, Dec. 1984, Medical Sciences, "Selective Killing of Leukemic Cells by Merocyanine 540-Mediated Photosensitization," Sieber et al.
Molecular Basis of Cancer, Part B: Macromolecular Recognition, Chemotherapy, and Immunology, pp. 227-234, 1985, Alan R. Liss, Inc., "Merocyanine 540-Mediated Photosensitization of Leukemia and Solid Tumor Cells," Sieber.
Cancer Research 46, pp. 2072-2076, Apr. 1986, "Dye-Mediated Photosensitization of Murine Neuroblastoma Cells," Sieber et al.
Blood, vol. 68, No. 1 (Jul.) 1986, pp. 32-36, "Dye Mediated Photolysis of Human Neuroblastoma Cells: Implications for Autologous Bone Marrow Transplantation," Sieber et al.
Minimal Residual Disease in Acute Leukemia, 1986, A. Habenbeek, B. Lowenberg (editors), Martinus Nijhoff Publishers, "Detection and Selective Destruction of Tumor Cells by the Lipophilic Dye, Merocyanine 540," pp. 282-294, Sieber.
Transfusion, vol. 26, No. 5, 1986, pp. 481-483, "Inactivation of Human T-Cell Lymphotropic Virus, Type III by Heat, Chemicals, and Irradiation," Quinnan et al.

Primary Examiner—Sidney Marantz
Attorney, Agent, or Firm—Quarles & Brady

[57] ABSTRACT

A method of inactivating viruses comprises bringing the viruses into contact with an effective amount of a photosensitizing agent which will bind to the viruses and/or virus infected cells, and then exposing the resulting mixture to visible light to excite and inactivate the viruses.

5 Claims, 1 Drawing Sheet

INACTIVATING ENVELOPED VIRUSES WITH A MEROCYANINE DYE

FIELD OF THE INVENTION

The present invention relates generally to the field of microbiology. More particularly, it relates to a photosensitization method for inactivating viruses.

BACKGROUND OF THE INVENTION

Viruses can cause human or animal diseases. The inability to effectively inactivate pathogenic viruses without adversely affecting their antigenic properties has made it difficult to make safe, effective vaccines for viral diseases. In addition, the presence of viruses can destroy the utility of valuable food and industrial products.

Heat treatments, the extraction of virus with solvents and detergents, and the treatment with high doses of gamma radiation can be effective means of inactivating viruses. However, those procedures are rigorous and nonspecific and their applicability is limited. As a result there is a need for a simple, effective method for inactivating viruses.

BRIEF SUMMARY OF THE INVENTION

It is an object of the present invention to disclose a simple, effective method of inactivating viruses.

It is a further object to disclose a method of inactivating viruses without adversely affecting their antigenicity. genicity.

It is a still further object to disclose photosensitizing agents for use in the methods.

Other objects will be apparent from the description which follows.

It has now been discovered that enveloped viruses and virus-infected cells, can be inactivated by bringing them into contact with an effective amount of a photosensitizing agent and exposing the resulting mixture to visible light until the viruses and virus-infected cells have been inactivated. It also has been discovered that the antigenic properties of the viruses are not adversely affected so that they can be used to prepare vaccines.

The method of the invention offers the following advantages:

1. It is selective. It inactivates viruses and virus-infected cells without adversely affecting other product components.
2. It is relatively non-toxic and excess photosensitizing agent can be easily removed.
3. It uses visible light.

The photosensitizing agents which are to be used in the method of the present invention are agents which preferentially bind to the lipids in enveloped viruses or virus-infected cells and which do not or bind only minimally to the other components of the products.

The agents which are preferred for use in the method are merocyanine dyes which are probably non-mutagenic and which have been used in the past as flourescent probes to study the structure and function of biological membranes (Cohen et al. J. Membr. Biol., 19, 1–36 (1974)). The merocyanine dyes, have been shown to undergo transient, voltage-dependent flourescence enhancements in response to electrical stimulation when they are incorporated into excitable membranes (Davila et al., Nature New Biol., 241, 159–160 (1973)). The generation of electrochemical potentials in human (Sims et al., Biochemistry, 13 3315–3330 (1974)) and Amphiuma red cell membranes (Hoffman and Laris, J. Physiol, 239. 519–552 (1974)), also enhance the fluorescence of some of these dyes. These probes have been success fully used in the detection of leukemic cells, Valinsky et al U.S. Pat. No. 4,424,201, and more recently for the selective killing of leukemic cells in bone marrow by agent-mediated photosensitization (Sieber et al., Proc. Natl. Acad. Sci. U.S.A. Vol 81, pp. 7584–7587 Dec. 1984).

The preferred agents are compounds of the formula

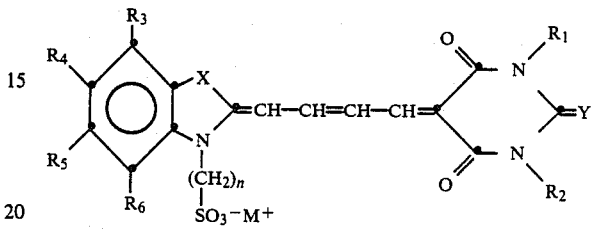

wherein n is 1–5; X is oxygen (O), sulphur (S), —CR$_1$-R$_2$—, or selenium (Se); Y is 0 or S; M is an alkaline metal or other basic group; R1 and R2 are the same or different alkyl groups of 1 to 8 carbons; and R3, R4, R5, and R6 are selected from hydrogen, lower alkyl groups of 1 to 5 carbons, lower alkoxy groups of 1 to 5 carbons, phenyl lower alkyls, such as phenylmethyl; or R3 and R4, or R4 and R5, or R5 and R6 are part of an aromatic ring.

The method of the invention may be practiced on either a continuous basis, or on a batch basis.

The light source for use with the method of the present invention includes any light source that will provide visible light of a suitable wave length for the desired length of time, including that disclosed in U.S. Pat. No. 4,321,919. Especially preferred is the light source of the photopheresis system available from the THERAKOS Division of Johnson & Johnson Cardiovascular of King of Prussia, Pa. under the trade name UVAR.

The exact mechanism of inactivation of viruses by the method of the present invention is not yet fully understood. The currently available data are compatible with the following model: The photosensitizing agent binds preferentially to disordered or cholesterol-free domains in lipid bilayers. Binding to proteins, carbohydrates and chromatin is minimal. High affinity binding sites for the agent appear to exist on the enveloped viruses and some virus-infected cells. Photoexcitation of membrane-bound agent molecules leads to the formation of reactive oxygen species, such as singlet oxygen, which cause lipid peroxidation. Secondary photoproducts may react with intracellular components.

Variables which can affect the method are agent concentration, protein concentration, protein composition, geometry and optical properties of the container, intensity and spectral properties of the light source and duration of the illumination. Those skilled in the art will appreciate that each of those variables can be varied within rather wide margins, provided the other variables are adjusted accordingly.

DESCRIPTION OF THE PREFERRED EMBODIMENT

Figure 1:
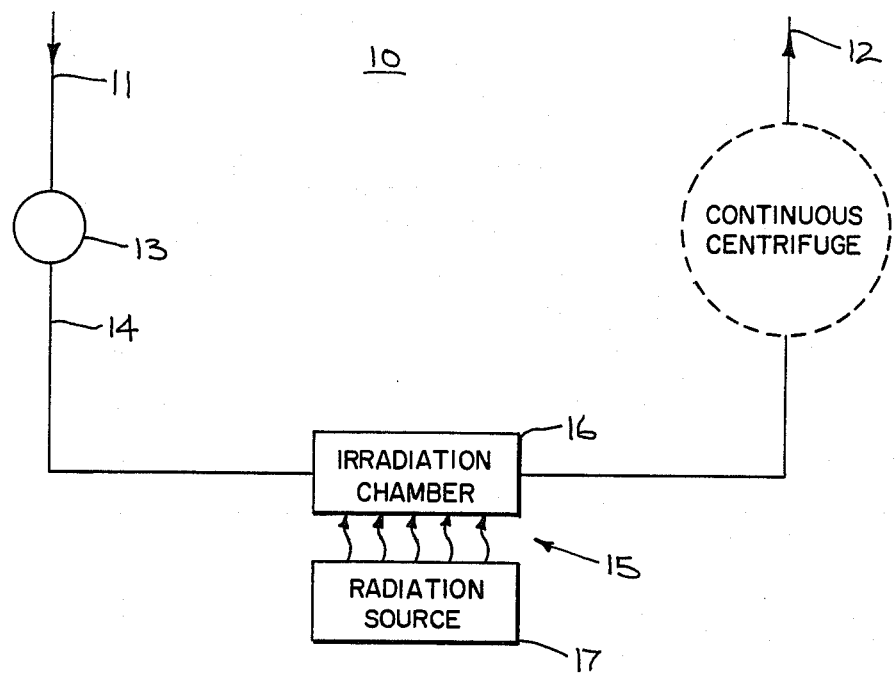
FIG. 1 is a schematic flow diagram illustrating a preferred embodiment of a system operating in accordance with the present invention.

In FIG. 1 herein a schematic diagram is shown of a system 10 for use with the method of the present invention.

As shown schematically in FIG. 1, in the system 10 a liquid product, such as a suspension, is passed on a continuous basis from inlet 11 to an outlet 12. When the method is continuous a typical flow rate is in range of from about 10 to 75 ml/min. with a preferred range being from about 40 to 50 ml/min. The desired flow rates are produced by a pump 13, which is positioned in the system as generally indicated at 14.

In the preferred mode of practicing the continuous mode of the method of the present invention, the photosensitizing agent is added to the product before introduction into the system or downstream of pump 13, and upstream of where the product enters the irradiation station 15.

The photosensitizing agent is usually first dissolved in the product in an amount which takes into account the flow rate and achieves a concentration of the agent in the product in the desired range as the product passes through the irradiation station 15.

At irradiation station 15, which consists of an irradiation chamber 16 and radiation source 17, the product containing the desired concentration of dissolved photosensitizing agent, is subjected to visible light and preferably visible light having the bulk of its spectral components in the preferred orange to green range for the activation of the particular photosensitive agent being employed in the treatment being conducted. The irradiation station 15 is constructed so as not to block radiation in the desired portion of the visible light spectrum and to prevent the product from being overheated and damaged.

Figure 2:
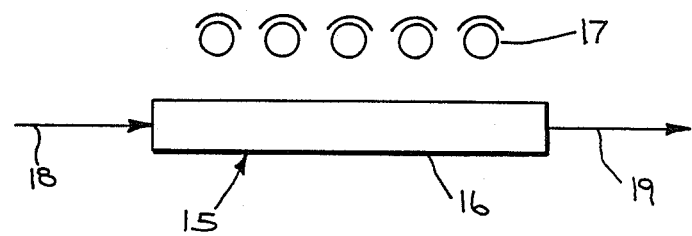
FIG. 2 is a schematic elevational view of the irradiation station portion of the FIG. 1 system.

In FIG. 2, a schematic view appears of an irradiation station 15 of a type suitable for use with the invention. The preferred station 15 consists of an irradiation chamber 16, having an inlet 18 and an outlet 19, enabling product flow through the chamber, and a spaced radiation source 17 of visible light. The chamber 16 can take various forms, with the principal requirement being that it have at least one wall which is substantially transparent to visible light. The chamber (or at least the transparent wall) therefore can be comprised of various substantially visible light transparent plastics, such as polyvinyl chloride and the like.

In the irradiation chamber 16, the product to be treated flows through a flow passage which is of relatively thin cross-section to insure ample exposure to the visible light e.g. about 2 mm thick. The total surface area of the flow passage in the chamber 16 is calculated to provide the product contained therein with the desired radiation dose level from the visible light source 17.

The visible light source 17 can comprise commercially available lamps, numerous types of which are known in the art. Especially preferred is an apparatus consisting of a plurality of fluorescent tubes with concentric jackets spaced from the tubes to form the flow passages for the product to be irradiated. By way of example, the light source can comprise a single 1000 watt Hg lamp of the type available from Oriel Corporation of Stamford, Conn., under Model designation 6287. When used with appropriate filters this source provides a good relatively continuous spectrum of high intensity radiation between 3200 and 4000 Angstroms, with a peak emission at about 3650 Angstroms, which is preferred when a merocyanine dye is the photosensitizing agent being employed in the method of the invention. The described lamp with a suitable reflector can be positioned approximately 50 to 30 cm from the flow passage. With the flow rates utilized in accordance with one aspect of the invention, such a source will provide the desired amount of absorbed energy in the flowing product for practicing the method of the invention.

Alternatively, the apparatus may take the form of a single batch container, containing the product and the photosensitizing agent, which can be treated with visible light.

When the product is in an aqueous environment the preferred excitation spectrum peaks are at 510 and 535 nm and in an organic phase, the spectrum is redshifted to 565 nm. After completion of the photosensitization step the excess agent may be separated by centrifugation. If desired, undesired components can be separated from the mixture by precipitation with solvents or salt, solvent extractions, or by chromatographic means.

Representative of the specific agents that can be used are the following:

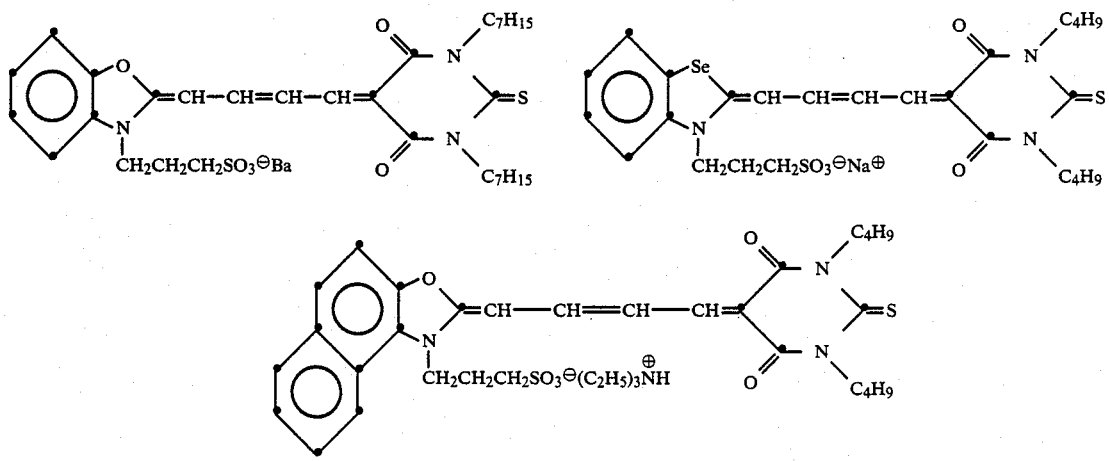

-continued

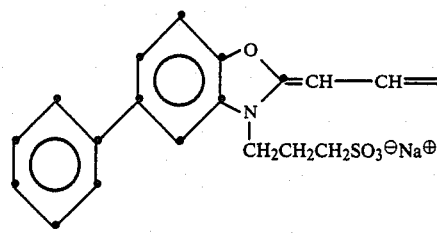
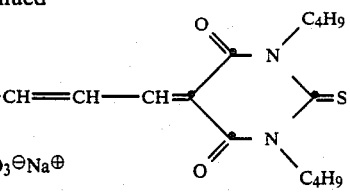

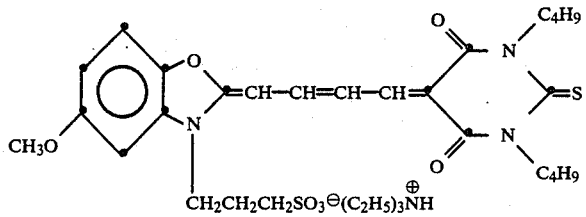
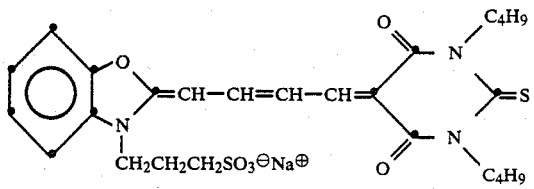

The photosensitizing agent is employed in an amount which is effective under the conditions of use to accomplish the inactivation of the viruses which may be present. Some of the agents, of course, are more active than others and can be used in smaller amounts. The toxicity of the preferred merocyanine dyes is very low. Therefore, it is not essential that they be completely removed from the treated product before it can be used in its normal manner.

The merocyanine, MC 540, is normally used with light of suitable wavelength in an amount of about 10 micrograms to about 25 micrograms per milliliter of product and a more active merocyanine derivative, MC 540A, is used in an amount of about 5 micrograms to about 10 micrograms per milliliter under comparable conditions.

The effective wavelengths of visible light that can be used vary greatly; however, it is generally desired that the light be of a wavelength in the green to orange range when the agent is a merocyanine dye. It appears that blue light and dark red light is not particularly effective with the preferred merocyanine dyes.

Tests have shown that:

(1) Suspensions of Friend virus, Friend virus-transformed cells, Herpes simplex, HTLV-I and HTLV-I infected cells are rapidly inactivated by MC 540-mediated photosensitization.

(2) The small amounts of dye that are transferred with the photosensitized products or plasma/serum components are not toxic to mice. The effective amount of the most active merocyanine derivative is about 100,000 times less than the $LD_{10}$ of the compound in mice.

The ability of MC 540 to react with enveloped (i.e. lipid-containing) viruses was tested with the Friend erythroleukemia virus complex, the human T cell leukemia virus, HTLV-I and Herpes simplex 1. Friend virus was obtained from cell-free supernatants of cultured erythroleukemia cells or as a cell-free extract from infected animals. Simultaneous exposure to MC 540 (15 μg/ml) and light (40 J/cm2) reduced the virus titer by $\geq 4$ logs regardless of the origin of the virus preparation. Virus-infected spleen cells, bone marrow cells, and cultured Friend erythroleukemia cells were inactivated at about the same rate as cell-free virus preparations.

HTLV-I was also susceptible to MC 540-mediated photosensitization. The amount of virus that could be sedimented by centrifugation was reduced 5-fold after treatment with MC 540 and light. The remaining 80% of the virus were probably lysed. The small fraction that was sedimented was visibly stained by MC 540. It is conceivable that the sedimented virus fraction, although not lysed, had sustained enough photodynamic damages to make it noninfectious. For example, when the virus is Herpes simplex 1 the order of magnitude reduction is as high as 45 times.

The demonstrated effectiveness of the method of the present invention in inactivating Herpes simplex 1 makes it possible to treat herpes lesions by applying or injecting MC 540 containing preparations onto or into the lesions.

The ability of the agents to photosensitize in such lower concentrations should make it possible to use the dyes or dermatological products which can be painted on or injected into viral containing lesions prior to exposure to visible light.

An analog of MC 540 which we have labeled MC 540A (see structural formula below) reduces illumination times about 6-fold when used in equimolar concentrations.

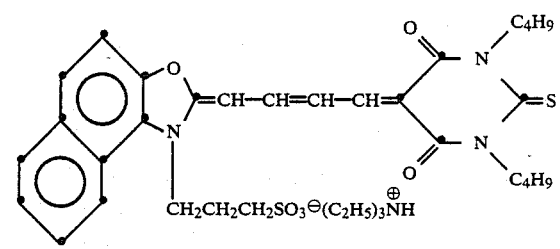

Merocyanine-mediated photolysis of viruses appears to be primarily mediated by singlet oxygen. An additional 2-fold reduction in illumination time can therefore be achieved by performing the photosensitization step in the presence of deuterium oxide ($D_2O$).

Unlike heat or high doses of ionizing irradiation, MC 540-mediated photolysis is more selective in its toxicity. Dye-mediated photosensitization may be the preferred antiviral treatment in situations where critical components are temperature or radiation sensitive. In addition, the acute systemic toxicity of dyes, such as MC 540, is very low. The amount of dye that is injected with a typical mouse bone marrow graft is more than 100,000 times less than the $LD_{10}$ in the same species.

Surprisingly, tests have shown that viruses inactivated by the method of the present invention retain their antigenic properties. Thus, it should be possible to make vaccines using the viruses inactivated by the method of the present invention.

Representative of the viruses which can be inactivated by the method of the present invention are those previously described, as well as, the viruses which cause human and animal diseases, such as bovine viral diarrhea, and viruses which infect bacterial products such as the Epsten Barr virus.

The invention is further illustrated by the following examples.

EXAMPLE 1

When cultured F4-6 erythroleukemia cells, spleen or marrow cells from diseased animals, cell-free extracts of cultured cells, spleen cells, or marrow cells, or cell-free supernatants of F-6 cultures were injected into healthy B6D2F1 mice, the spleen weights increased from 70 mg to about 2 g within two weeks. The animals became polycythemic and, eventually, died. When cell suspensions, cell-free extracts, or culture supernatants were photosensitized and exposed to light prior to injection, spleen weights remained normal, hematocrits remained normal, and the animals survived. Normal pluripotent hematopoietic stem cells (as determined by the ability of photosensitized marrow cells to rescur lethally irradiated syngeneic hosts) were spared by the photosensitization treatment. Virus preparations that were exposed to dye or light alone caused splenomegaly, polycythemia, and death. A series of experiments thus showed that MC 540-mediated photolysis inactivates free Friend virus, intracellular Friend virus, and Friend virus-infected cells.

EXAMPLE 2

Experiments with human herpes simplex virus type 1 (HSV-1), and human T-cell leukemia virus type I (HTLV-I) produced similar results. Herpes simplex-1 was extremely susceptible to MC 540 mediated photolysis. A limiting dilution plaque forming assay on Vero cells indicated a $\geq 5$ log reduction (limit of detection) of the virus titer after only 10 min. of illumination. The standard illumination protocol calls for 90 min. of illumination. It is thus conceivable that the titer can be reduced by $\geq 45$ log. Infectivity assays for HTLV-I have, unfortunately, not yet been developed. We therefore used reverse transcriptase activity as an indicator of virus destruction. Photosensitized and untreated aliquots of the same virus suspension were pelleted on a sucrose cushion. The pellet of the treated aliquot was about 5 times smaller and visibly red. Its reverse transcriptase content was reduced by more than 80% (Table 1). The balance of the enzyme activity was recovered in the supernatant. More than 80% of the original virus mass was apparently damaged so extensively (virtually "dissolved") that it was no longer pelletable by a two hour spin at $100,000 \times g$. If the photosensitization of enveloped viruses bears any resemblance to the photosensitization of cells, it is reasonable to speculate that the pelletable material was also photodamaged and perhaps no longer infective.

TABLE 1

| HTLV-I, Reverse Transcriptase activity | |
|---|---|
| (1) No dye, no light | 194,268 cpm |
| (2) MC 540, no light | 208,548 cpm |
| (3) No dye, light 90 min | 158,016 cpm |
| (4) MC 540, light 90 min | 37,848 cpm |

EXAMPLE 3

The acute systemic toxicity of MC 540 was determined by injecting groups of 10 BAF1 mice intravenously with graded doses of MC 540. Survival data were plotted on a log probit scale and fitted with a least square regression line to determine and $LD_{10}$ and $LD_{50}$ (Table 2). It should be pointed out that MC 540 is not more toxic than the fluorescent dyes that are commonly used for the angiography of the retina. Necropsies showed that the probable cause of death after high doses of MC 540 was the formation of large emboli of precipitated dye in major blood vessel (i.e. we killed the mice by exceeding the solubility of the dye in plasma).

TABLE 2

| Acute Toxicity of MC 540 | |
|---|---|
| $LD_{10}$ (mouse) | 55 mg/kg |
| $LD_{50}$ (mouse) | 84 mg/kg |
| Injected with photosensitized marrow graft | 0.0004 mg/kg |
| For comparison | |
| $LD_{50}$ (mouse) fluorescein | 300 mg/kg |
| $LD_{50}$ (mouse) indocyanine green | 70 mg/kg |

It will be appreciated by those skilled in the art that the method of the present invention will make it possible for biologicals, such as pure bacterial cultures, culture mediums and the like to be supplied viral-free.

It is not presently known exactly which viruses of the many identified can be effectively inactivated by the method of the present invention. However, those skilled in the art should be able to apply the method to specific viruses without undue experimentation.

It will be readily understood by those skilled in the art that the foregoing description has been for purposes of illustration only and that a number of changes may be made without departing from the scope of the invention. Therefore, it is intended that the invention not be limited except by the claims.

I claim:

1. The method of inactivating an enveloped virus which comprises first bringing said enveloped virus into contact with an effective amount of a photosensitizing agent to inactivate said virus, said agent being a merocyanine dye which selectively binds to said virus and then exposing the combination of the virus and agent to visible light of sufficient strength for a sufficient period of time to photosensitize and inactive the virus.

2. The method of claim 1 in which the merocyanine dye is a compound of the following formula:

3. A method of claim 1 in which the merocyanine dye is selected from the group consisting of the following:

[Structures of merocyanine dyes shown]

4. A method of inactivating an enveloped vircus without affecting its usefulness in making a vaccine whyich comprises bringing the virus into contact with an effective amount of a merocyanine dye photosensitizing agent to inactivate the virus and then subjecting the virus and photosensitizing agent to an effective amount of visible light for a sufficient length of time to inactivate the virus without affecting its usefulness in making a vaccine.

5. A method treating a disease which is caused by an enveloped virus, which disease results in lesions, said method comprising forming a combination of the enveloped virus in the lesions and an effective amount of a merocyanine dye photosensitizing agent to inactivate the virus and then exposing the combination to an effective amount of visible light for a sufficient length of time to inactivate said virus.

in which n is 1-5; X is oxygen, sulphur, $-CR_1R_2-$, or selenium; Y is O or S; M is an alkaline metal basic group; $R_1$ and $R_2$ are the same or different alkyl groups of 1 to 8 carbons; and $R_3$, $R_4$, $R_5$ and $R_6$ are selected from hydrogen, lower alkyl groups of 1 to 5 carbons, lower alkoxy groups of 1 to 5 carbons, phenyl lower alkyls; and an aromatic ring formed by $R_3$ and $R_4$, or $R_4$ and $R_5$ or $R_5$ and $R_6$.

* * * * *

UNITED STATES PATENT AND TRADEMARK OFFICE
CERTIFICATE OF CORRECTION

PATENT NO. : 4,775,625

DATED : October 4, 1988

INVENTOR(S) : Sieber

It is certified that error appears in the above-identified patent and that said Letters Patent is hereby corrected as shown below:

| | |
|---|---|
| Column 1, line 31 | delete "genicity." |
| Column 2, line 4 | "success fully" should read --successfully-- |
| Column 5, line 62 | "$\geqq$" should read -- $\geq$ -- |
| Column 7, line 47 | "$\geqq$" should read -- $\geq$ -- |
| Column 7, line 51 | "$\geqq$" should read -- $\geq$ -- |
| Column 8, line 17 | after "determine" delete "and" |
| Column 10, line 48 | "vircus" should read --virus-- |
| Column 10, line 50 | "whyich" should read --which-- |

Signed and Sealed this

Twelfth Day of December, 1989

*Attest:*

JEFFREY M. SAMUELS

*Attesting Officer*     *Acting Commissioner of Patents and Trademarks*

UNITED STATES PATENT AND TRADEMARK OFFICE
CERTIFICATE OF CORRECTION

PATENT NO. : 4,775,625

DATED : October 4, 1988

INVENTOR(S) : Sieber

It is certified that error appears in the above-identified patent and that said Letters Patent is hereby corrected as shown below:

Column 1, line 4: Insert the following as the first paragraph:

--This invention was made with government support under Federal Grant 5ROI CA-42734-06 awarded by the National Institutes of Health. The government has certain rights in the invention.--

Signed and Sealed this

Twentieth Day of April, 1993

*Attest:*

MICHAEL K. KIRK

*Attesting Officer*     *Acting Commissioner of Patents and Trademarks*